United States Patent [19]

Johnson

[11] 4,150,222

[45] Apr. 17, 1979

[54] (5E)-9-DEOXY-6,9-EPOXY-PROSTAGLANDIN DERIVATIVES

[75] Inventor: Roy A. Johnson, Kalamazoo, Mich.

[73] Assignee: The Upjohn Company, Kalamazoo, Mich.

[21] Appl. No.: 912,552

[22] Filed: Jun. 5, 1978

Related U.S. Application Data

[63] Continuation of Ser. No. 775,003, Mar. 7, 1977, abandoned.

[51] Int. Cl.² ........................................... C07D 307/93
[52] U.S. Cl. .............................. 542/426; 260/346.22; 260/346.73; 542/429
[58] Field of Search ..................... 260/346.22, 346.73; 542/426, 429

[56] References Cited

PUBLICATIONS

Johnson et al., J.A.C.S., 99, p. 4182 (1977).
Johnson et al., Prostaglandins vol. 12 (6), pp. 915–928, Dec. 1976.
Pace–Asciak et al., Biochemistry, vol. 10 (20), pp. 3657–3664 (1971).

*Primary Examiner*—Natalie Trousof
*Assistant Examiner*—Bernard Dentz
*Attorney, Agent, or Firm*—Morris L. Nielsen

[57] ABSTRACT

Prostaglandin (PG₁) derivatives having a 9-deoxy-6,9-epoxy feature together with either a 5-halo or 5,6-didehydro feature are disclosed, for example

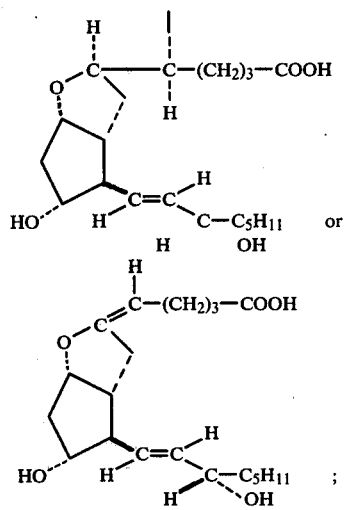

including processes for preparing them and the appropriate intermediates; said derivatives having pharmacological activity.

18 Claims, 1 Drawing Figure

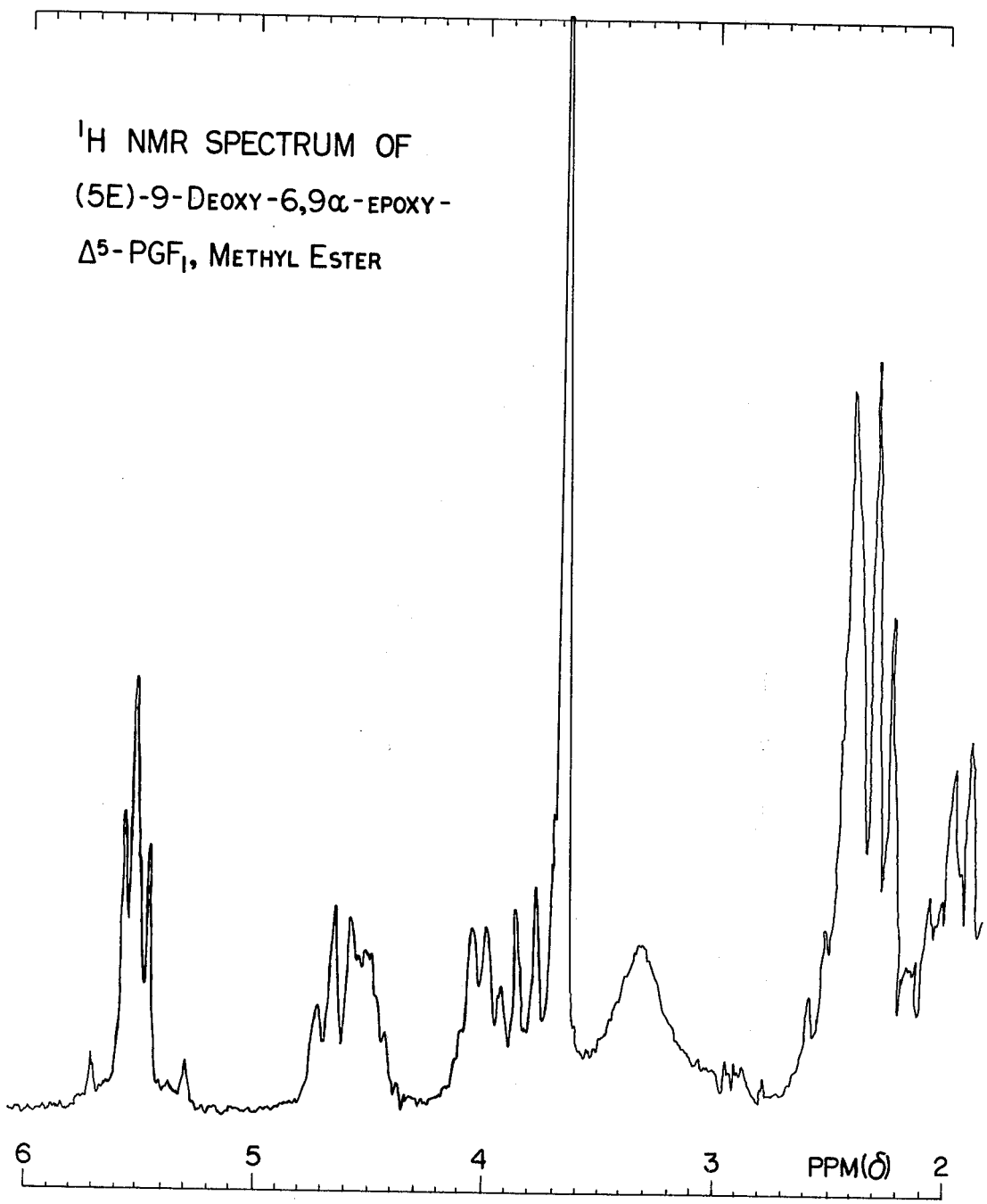

(5E)-9-DEOXY-6,9-EPOXY-PROSTAGLANDIN DERIVATIVES

This is a continuation of application Ser. No. 775,003, filed Mar. 7, 1977 and now abandoned.

BACKGROUND OF THE INVENTION

This invention relates to derivatives of prostaglandins, more specifically certain 9-deoxy-6,9-epoxy derivatives of specific stereo configuration, and to processes for preparing them.

The prostaglandins and analogs are well-known organic compounds derived from prostanoic acid which has the following structure and atom numbering:

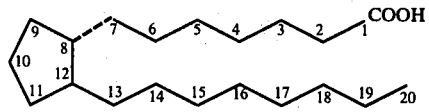

As drawn hereinafter the formulas represent a particular optically active isomer having the same absolute configuration as $PGE_1$ obtained from mammalian tissues.

In the formulas, broken line attachments to the cyclopentane ring or side chain indicate substituents in alpha configuration, i.e. below the plane of the ring or side chain. Heavy solid line attachments indicate substituents in beta configuration, i.e. above the plane.

For background, see for example Bergstrom et al., Pharmacol. Rev. 20, 1 (1968) and Pace-Asciak et al., Biochem. 10, 3657 (1971).

SUMMARY OF THE INVENTION

It is the purpose of this invention to provide novel products having pharmacological activity. It is a further purpose to provide processes for preparing these products and their intermediates.

Accordingly, there are provided enol ethers of the formula:

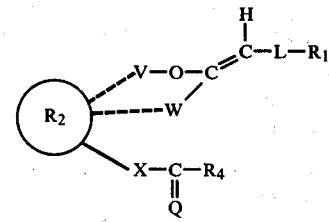

wherein $R_2$ is

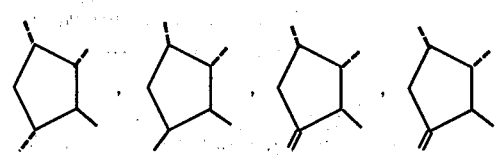

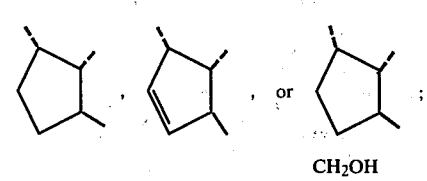

wherein L is (1) $-(CH_2)_d-C(R_{22})_2$
(2) $-CH_2-O-CH_2-Y-$ or
(3) $-CH_2CH=CH-$ wherein d is zero to 5; $R_{22}$ is hydrogen, methyl, or fluoro, being the same or different with the proviso that one $R_{22}$ is not methyl when the other is fluoro; and Y is a valence bond or $-(CH_2)_k-$ wherein k is one or 2;

wherein Q is

wherein $R_8$ is hydrogen or alkyl of one to 4 carbon atoms, inclusive;

wherein $R_1$ is (1) $-COOR_3$
(2) $-CH_2OH$
(3) $-CH_2N(R_9)_2$ (4) 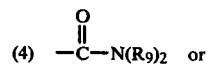

(5) 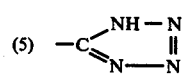

wherein $R_3$ is (a) alkyl of one to 12 carbon atoms, inclusive, (b) cycloalkyl of 3 to 10 carbon atoms, inclusive, (c) aralkyl of 7 to 12 carbon atoms, inclusive, (d) phenyl, (e) phenyl substituted with one, 2, or 3 chloro or alkyl of one to 4 carbon atoms, inclusive;

(f) 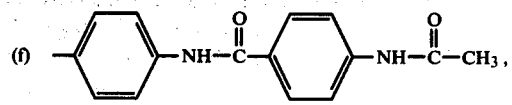

(g) 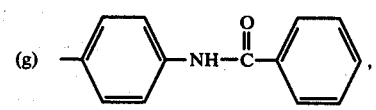

(h) 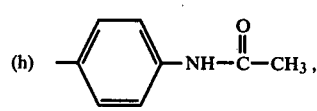

(i) 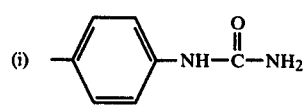

(j) 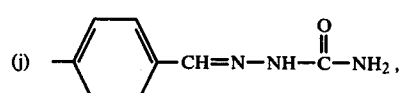

(k) 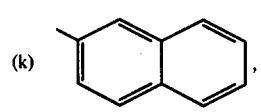

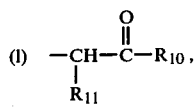

wherein R₁₀ is phenyl, p-bromophenyl, p-biphenylyl, p-nitrophenyl, p-benzamidophenyl, or 2-naphthyl; and wherein R₁₁ is hydrogen or benzoyl; (m) hydrogen, or (n) a pharmacologically acceptable cation; and wherein R₉ is hydrogen or alkyl of one to 4 carbon atoms, inclusive, being the same or different: wherein R₄ is

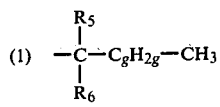

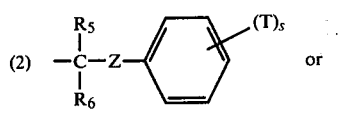

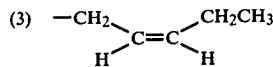

wherein $C_gH_{2g}$ is alkylene of one to 9 carbon atoms, inclusive, with one to 5 carbon atoms, inclusive, in the chain between —CR₅R₆— and terminal methyl, wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro and the further proviso that neither R₅ nor R₆ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between CR₅R₆— and the phenyl ring; wherein T is alkyl of one to 4 carbon atoms, inclusive, fluoro, chloro, trifluoromethyl, or —OR₇— wherein R₇ is alkyl of one to 4 carbon atoms, inclusive, and s is zero, one, 2 or 3, with the proviso that not more than two T's are other than alkyl and when s is 2 or 3 the T's are either the same or different;

wherein V is a valence bond or methylene; wherein W is —(CH₂)ₕ— wherein h is one or two; and wherein X is
(1) trans—CH=CH—
(2) cis—CH=CH—
(3) —C≡C— or
(4) —CH₂CH₂—;
including the lower alkanoates thereof.

There are likewise provided halo ethers of the formula

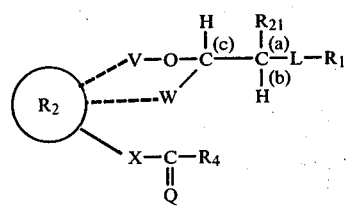

II wherein (a), (b), and (c) represent valence bonds such that when (a) is alpha, (b) and (c) are both beta, and when (a) is beta, (b) and (c) are both alpha;

wherein ⓡ₂ is

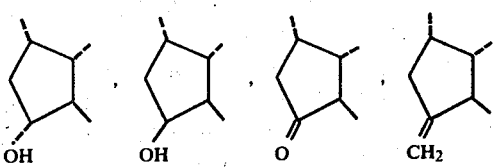

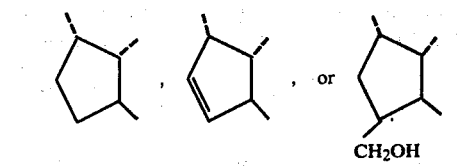

wherein L is
(1) —(CH₂)d—C(R₂₂)₂
(2) —CH₂—O—CH₂—Y— or
(3) —CH₂CH=CH— wherein d is zero to 5; R₂₂ is hydrogen, methyl, or fluoro, being the same or different with the proviso that one R₂₂ is not methyl when the other is fluoro; and Y is a valence bond or —(CH₂)k—
wherein k is one or 2;
wherein Q is

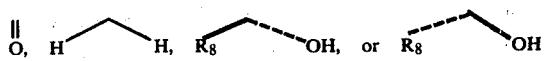

wherein R₈ is hydrogen or alkyl of one to 4 carbon atoms, inclusive;
wherein R₁ is
(1) —COOR₃
(2) —CH₂OH
(3) —CH₂N(R₉)₂

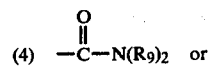

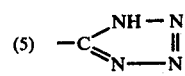

wherein R₃ is a (a) alkyl of one to 12 carbon atoms, inclusive, (b) cycloalkyl of 3 to 10 carbon atoms, inclusive, (c) aralkyl of 7 to 12 carbon atoms, inclusive, (d) phenyl, (e) phenyl substituted with one, 2, or 3 chloro or alkyl of one to 4 carbon atoms, inclusive;

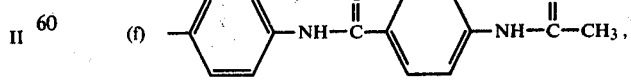

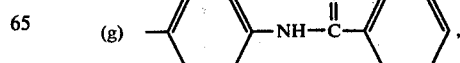

(h) 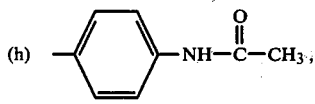

(i) 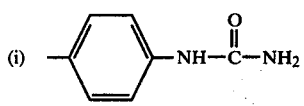

(j) 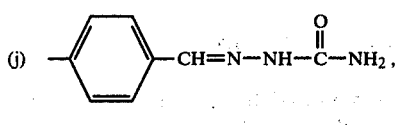

(k) 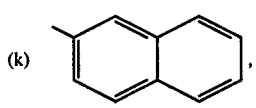

(l) 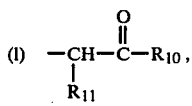

wherein $R_{10}$ is phenyl, p-bromophenyl, p-biphenylyl, p-nitroohenyl, p-benzamidophenyl, or 2-naphthyl; and wherein $R_{11}$ is hydrogen or benzoyl; (m) hydrogen, or (n) a pharmacologically acceptable cation; and wherein $R_9$ is hydrogen or alkyl of one to 4 carbon atoms, inclusive, being the same or different; wherein $R_4$ is (1) 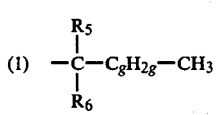

(2) 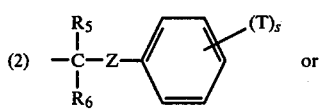 or (3) 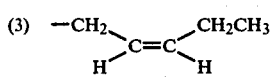

wherein $C_gH_{2g}$ is alkylene of one to 9 carbon atoms, inclusive, with one to 5 carbon atoms, inclusive, in the chain between $-CR_5R_6-$ and terminal methyl, wherein $R_5$ and $R_6$ are hydrogen, alkyl of one to 4 carbon atoms, inclusive, or fluoro, being the same or different, with the provison that one of $R_5$ and $R_6$ is fluoro only when the other is hydrogen or fluoro and the further proviso that neither $R_5$ nor $R_6$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_5R_6-$ and the phenyl ring; wherein T is alkyl of one to 4 carbon atoms, inclusive, fluoro, chloro, triflouromethyl, or $-OR_7-$ wherein $R_7$ is alkyl of one to 4 carbon atoms, inclusive, and s is zero, one, 2 or 3, with the proviso that not more than two T's are other than alkyl and when s is 2 or 3 the T's are either the same or different;

wherein V is a valence bond or methylene; wherein W is $-(CH_2)_h-$ wherein h is one or two; wherein $R_{21}$ is iodo, bromo, chloro, or fluoro, and wherein X is
(1) trans—CH=CH—
(2) cis—CH=CH—
(3) —C≡C— or
(4) —CH₂CH₂—

Within the scope of the prostaglandin derivatives described herein there are represented (a) $PGF_\alpha$ compounds when (R₂) is

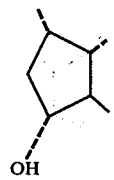

(b) $11\beta\text{-}PGF_\alpha$ compounds when (R₂) is

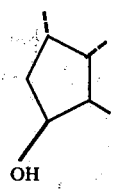

(c) 11-Deoxy-11-keto-$PGF_\alpha$ compounds when (R₂) is

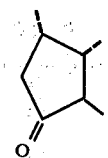

(d) 11-Deoxy-11-methylene-$PGF_\alpha$ compounds when (R₂)

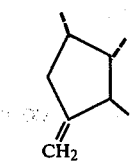

(e) 11-Deoxy-$PGF_\alpha$ compounds when (R₂) is

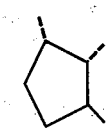

(f) 11-Deoxy-10,11-Didehydro-$PGF_\alpha$ compounds when (R₂) is

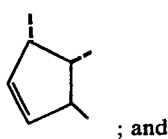

(g) 11-Deoxy-11-hydroxymethyl-PGF$_\alpha$ compounds when (R$_2$) is

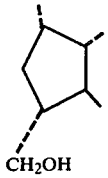

Formula II includes compounds of the formula

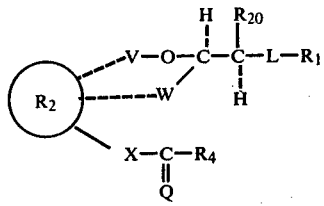

III and

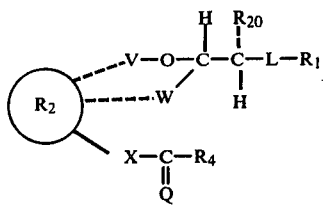

IV

A typical example of the compounds of formula I is represented by the formula

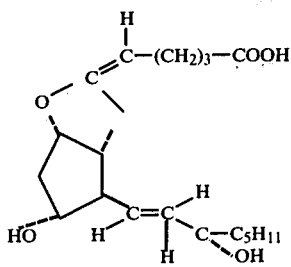

V and is named as a derivative of PGF$_1$: (5E)-9-deoxy-6,9$\alpha$-epoxy-$\Delta^5$PGF$_1$.

A typical example of the compounds of formula III is represented by the formula:

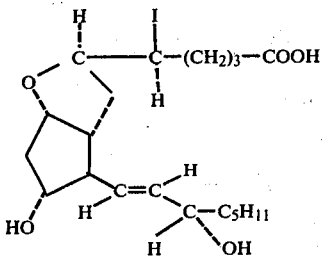

VI and is named (5S,6R)-5-iodo-9-deoxy-6,9$\alpha$-epoxy-PGF$_1$.

A typical example of the compounds of formuls IV is represented by the formula:

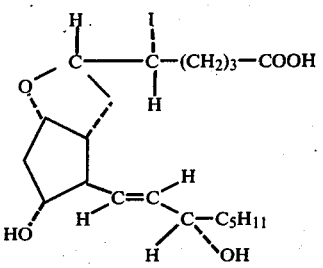

VII and is named (5R,6S)-5-iodo-9-deoxy-6,9$\alpha$-epoxy-PGF$_1$.

The above examples V, VI, and VII are species of the respective formula I, III, and IV compounds wherein (R$_2$) is

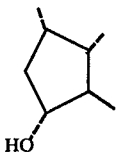

L is —(CH$_2$)$_3$—, Q is

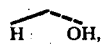

R$_1$ is —COOH, R$_4$ is n-pentyl, V is a valence bond, W is —CH$_2$—, and X is trans —CH=CH—.

The nomenclature for the above compounds and those identified hereinafter follows the conventions applied to prostaglandin-type compounds, See N. A. Nelson, J. Med. Chem. 17, 911 (1974). For "R" and "S" usage see R. S. Cahn, J. Chem. Ed. 41, 116 (1964). For "E" and "Z" designations of double bond stereoisomerism see J. E. Blackwood et al., J. Am. Chem. Soc. 90, 509 (1968).

The formula-I enol ethers are named as derivatives of PGE$_1$, regardless of the variations in either of the side chains, V and W in the heterocyclic ring, or the cyclopentane ring system represented by (R$_2$), following the conventions known and used in the prostaglandin art. Likewise, the formula-II, -III, and -IV halo ethers are named as derivatives of PGF$_1$. In formulas I-IV as used herein, W is bonded to the cyclopentane ring at the C-8 position, V at the C-9 position, and X at the C-12 position.

The products of this invention, represented herein by formulas I, II, III, and IV, are extremely potent in causing various biological responses. For that reason, these compounds are useful for pharmacological purposes. A few of those biological responses are: inhibitor of blood platelet aggregation, stimulation of smooth muscle, systemic blood pressure lowering, inhibiting gastric secretion and reducing undesirable gastrointestinal effects from systemic administration of prostaglandin synthetase inhibitors.

Because of these biological responses, these novel compounds are useful to study, prevent, control, or alleviate a wide variety of diseases and undesirable physiological conditions in mammals, including humans, useful domestic animals, pets, and zoological specimens, and in laboratory animals, for example, mice, rats, rabbits, and monkeys.

These compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., Intravenously, subcutaneously, intramuscularly, and in the form of sterile implants for prolonged action. For rapid response, especially in emergency situations, the intravenous route of administration is preferred. Doses in the range about 0.01 to about 10 mg. per kg. of body weight per day are used, the exact dose depending on the age, weight, and condition of the patient or animal, and on the frequency and route of administration.

The addition of these compounds to whole blood provides in vitro applications such as, storage of whole blood to be used in heart-lung machines. Additionally whole blood containing these compounds can be circulated through organs, e.g. heart and kidneys, which have been removed from a donor prior to transplant. They are also useful in preparing platelet rich concentrates for use in treating thrombocytopenia, chemotherapy, and radiation therapy. In vitro applications utilize a dose of 0.001–1.0 µg/ml of whole blood.

These compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, they are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the compound is administered by intravenous infusion immediately after abortion or delivery at a dose in the range about 0.01 to about 50 µg. per kg. of body weight per minute until the desired effect is obtained. subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

These compounds are useful as hypotensive agents to reduce blood pressure in mammals, including man. For this purpose, the compounds are administered by intravenous infusion at the rate about 0.01 to about 50 µg. per kg. of body weight per minute or in single or multiple doses of about 25 to 500 µg. per kg. of body weight total per day.

These prostaglandin derivatives are also useful in mammals, including man and certain useful animals, e.g., dogs and pigs, to reduce and control excessive gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 µg. to about 20 µg. per kg. of body weight per minute, or in a total daily dose by injection or infusion in the range about 0.01 to about 10 mg. per kg. of body weight per day, the exact dose depending on the age, weight, and condition of the patient or animal, and on the frequency and route of administration.

These compounds are also useful in reducing the undesirable gastrointestinal effects resulting from systemic administration of anti-inflammatory prostaglandin synthetase inhibitors, and are used for that purpose by concomitant administration of the prostaglandin derivative and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rate is inhibited by concomitant oral administration of certain prostaglandins of the E and A series, including $PGE_1$, $PGE_2$, $PGE_3$, 13,14-dihydro-$PGE_1$, and the corresponding 11-deoxy-PGE and PGA compounds. Prostaglandins are useful, for example, in reducing the undesirable gastrointestinal effects resulting from systemic administration of indomethacin, phenylbutazone, and aspirin. These are substances specifically mentioned in Partridge et al. as non-steroidal, anti-inflammatory agents. These are also known to be prostaglandin synthetase inhibitors.

The anti-inflammatory synthetase inhibitor, for example indomethacin, aspirin, or phenylbutazone is administered in any of the ways known in the art to alleviate an inflammatory condition, for example, in any dosage regimen and by any of the known routes of systemic administration.

The prostaglandin derivative is administered along with the anti-inflammatory prostaglandin synthetase inhibitor either by the same route of administration or by a different route. For example, if the anti-inflammatory substance is being administered orally, the prostaglanding derivative is also administered orally, or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin derivative is also administered rectally. Further, the prostaglandin derivative can be conveniently administered orally or, in the case of women, vaginally. It is especially convenient when the administration route is to be the same for both anti-inflammatory substance and prostaglandin derivative, to combine both into a single dosage form.

The dosage regimen for the prostaglandin derivative in accord with this treatment will depend upon a variety of factors, including the type, age, weight, sex and medical condition of the mammal, the nature and dosage regimen of the anti-inflammatory synthetase inhibitor being administered to the mammal, the sensitivity of the particular prostaglandin derivative to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostaglandin derivative to reduce and then substantially to eliminate those undesirable effects.

These compounds are also useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchietasis, pneumonia and emphysema. For these purposes, these compounds are administered in a variety of dosage forms, e.g., orally in the form of tablets, capsulses, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other anti-asthamtic agents, such as sympathomimetics (isoproterenol, phenylephrine, ephedrine, etc.); xanthine derivatives (theophylline and aminophylline); and corticosteroids (ACTH and prednisolone).

These compounds are effectively administered to human asthma patients by oral inhalation or by aerosol inhalation.

For administration by the oral inhalation route with conventional nebulizers or by oxygen aerosolization it is convenient to provide the instant active ingredient in dilute solution, preferably at concentrations of about 1 part of medicament to form about 100 to 200 parts by weight of total solution. Entirely conventional additives may be employed to stabilize these solutions or to provide isotonic media, for example, sodium chloride, sodium citrate, citric acid, sodium bissulfite, and the like can be employed.

For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizer. Instead of a co-solvent there can also be used a dispensing agent such as oleyl alcohol. Suitable means to employ the aerosol inhalation therapy technique are described fully in U.S. Pat. No. 2,868,691 for example.

These compounds are useful in mammals, including man, as nasal decongestants and are used for this purpose in a dose range of about 10 μg. to about 10 mg. per ml. of a pharmacologically suitable liquid vehicle or as an aerosol spray, both for topical application.

These compounds are also useful in treating peripheral vascular disease in humans. The term peripheral vascular disease as used herein means disease of any of the blood vessels outside of the heart and to disease of the lymph vessels, for example, frostbite, ischemic cerebrovascular disease, artheriovenous fistulas, ischemic leg ulcers, phlebitis, venous insufficiency, gangrene, hepatorenal syndrome, ductus arteriosus, non-obstructive mesenteric ischemia, arteritis lymphangitis and the like. These examples are included to be illustrative and should not be construed as limiting the term peripheral vascular disease. For these conditions the compounds of this invention are administered orally or parenterally via injection or infusion directly into a vein or artery, intra-venous or intra-arterial injections being preferred. The dosages of these compounds are in the range of 0.01–1.0 μg./kg. administered by infusions at an hourly rate or by injection on a daily basis, i.e. 1–4 times a day, the exact dose depending on the age, weight, and condition of the patient and on the frequency and route of administration. Treatment is continued for one to five days, although three days is ordinarily sufficient to assure long-lasting therapeutic action. In the event that systemic or side effects are observed the dosage is lowered below the threshold at which such systemic or side effects are observed.

These compounds are accordingly useful for treating peripheral vascular diseases in the extremities of humans who have circulatory insufficiencies in said extremities, such treatment affording relief of rest pain and induction of heating of ulcers.

For a complete discussion of the nature of and clinical manifestations of human peripheral vascular disease and the method previously known of its treatment with prostaglandins see South African Patent No. 74/0149 referenced as Derwent Farmdoc No. 58,400V. See Elliott, et al., Lancet, Jan. 18, 1975, pp. 140–142.

These compounds are useful in place of oxytocin to induce labor in pregnant female animals, including man, cows, sheep, and pigs, at or near term, or in pregnant animals with intrauterine death of the fetus from about 20 weeks to term. For this purpose, the copound is infused intravenously at a dose of 0.01 to 50 μg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor haas not yet started. An alternative route of administration is oral.

These compounds are further useful for controlling the reproductive cycle in menstruating female mammals, including humans. By the term menstruating female mammals is meant animals which are mature enough to menstruate, but not so old that regular menstruation has ceased. For that purpose the prostaglandin derivative is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

These compounds are further useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful for diagnostic procedures where dilation is necessary for tissue examination. For these purposes, the prostaglandin derivative is administered locally or systemically.

The prostaglandin derivative, for example, is administered orally or vaginally at doses of about 5 to 50 mg. per treatment of an adult female human, with from one to five treatments per 24 hour period. Alternatively the compound is administered intramuscularly or subcutaneously at doses of about one to 25 mg. per treatment. The exact dosages for these purposes depend on the age, weight, and condition of the patient or animal.

These compounds are further useful in domestic animals as an abortifacient (especially for feedlot heifers), as an aid to estrus detection, and for regulation or synchronization of estrus. Domestic animals include horses, cattle, sheep, and swine. The regulation or synchronization of estrus allows for more efficient management of both conception and labor by enabling the herdsman to breed all his females in short pre-defined intervals. This synchronization results in a higher percentage of live births than the percentage achieved by natural control. The prostaglandin is injected or applied in a feed at doses of 0.1–100 mg. per animal and may be combined with other agents such as steroids. Dosing schedules will depend on the species treated. For example, mares are given the prostaglandin derivative 5 to 8 days after ovulation and return to estrus. Cattle are treated at regular intervals over a 3 week period to advantageously bring all into estrus at the same time.

These compounds increase the flow of blood in the mammalian kidney, thereby increasing volume and electrolyte content of the urine. For that reason, these compounds are useful in managing cases of renal dysfunction, especially those involving blockage of the renal vascular bed. Illustratively, these compounds are useful to alleviate and correct cases of edema resulting, for exaple, from massive surface burns, and in the management of shock. For these purposes, these compounds are preferably first administered by intravenous injection at a dose in the range 10 to 1000 $\mu$g. per kg. of body weight or by intravenous infusion at a dose in the range 0.1 to 20 $\mu$g. per kg. of body weight per minute until the desired effect is obtained. Subsequent doses are given by intravenous, intramuscular, or subcutaneous injection or infusion in the range 0.05 to 2 mg. per kg. of body weight per day.

These prostaglandin derivatives ae useful for treating proliferating skin diseases of man and domesticated animala, including psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun-induced keratosis, non-malignant keratosis, acne, and seborrheic dermatitis in humans and atopic dermatitis and mange in domesticated animals. These compounds alleviate the symptoms of these proliferative skin diseases: psoriasis, for example, being alleviated when a scale-free psoriasis lesion is noticeably decreased in thickness or noticeably but incompletely cleared or completely cleared.

For these purposes, these compounds are applied topically as compositions including a suitable pharmaceutical carrier, for example as an ointment, lotion, paste, jelly, spray, or aerosol, using topical bases such as petrolatum, lanolin, polyethylene glycols, and alcohols. These compounds, as the active ingredients, constitute from about 0.1% to about 15% by weight of the composition, preferably from about 0.5% to about 2%. In addition to topical administration, injection may be employed, as intradermally, intra- or perilesionally, or subcutaneously, using appropriate sterile saline compositions.

These compounds are useful as antiflammatory agents for inhibiting chronic inflammation in mammals including the swelling and other unpleasant effects thereof using methods of treatment and dosages generally in accord with U.S. Pat. No. 3,885,041, which patent is incorporated herein by reference.

These enol-ether and halo ether compounds of this invention cause many of the biological responses known for the older prostaglandin compounds. In addition, they are surprisingly more specific with regard to potency and have a substantially longer duration of biological activity. They have the further advantage that they may be administered effectively orally, sublingually, intravaginally, buccally, or rectally as well as by the usual methods. Each of these novel analogs is therefore useful in place of the known prostaglandin $F_\alpha$-type compounds for at least one of the pharmacological purposes known for them, and is surprisingly and unexpectedly more useful for that purpose because it has a different and narrower spectrum of biological activity than the known prostaglandin, and therefore is more specific in its activity and causes smaller and fewer undesired side effects than the known prostaglandin. Moreover, because of its prolonged activity, fewer and smaller doses of these novel compounds can frequently be used to attain the desired result.

There are further provided the various processes for preparing the enol ethers of formula I and the halo ethers of formulas II–IV.

Thus, for the formula-I enol ether compounds, one process comprises the steps of starting with a compound of the formula

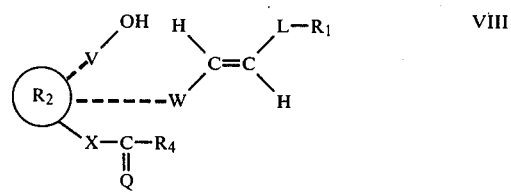

VIII wherein L, Q, R₁, (R₂), R₄, V, W, and X are as defined above, and (a) halogenating and cyclizing to form halo compounds of the formula

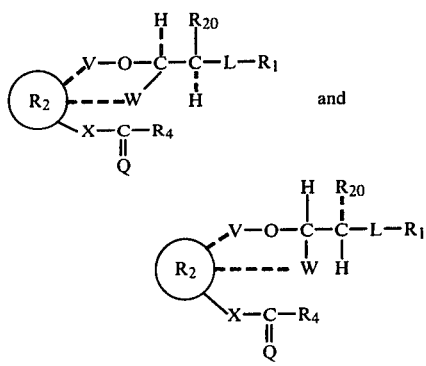

wherein L, Q, R₁, (R₂), R₄, V, W, and X are as defined above, and (a) halogenating and cyclizing to form halo compounds of the formula

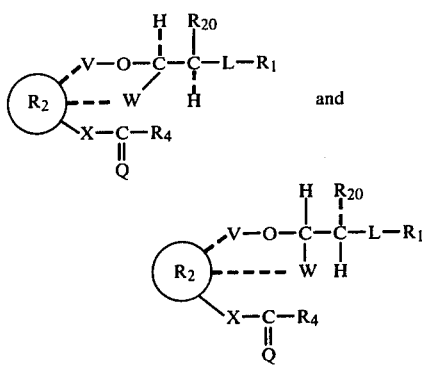

wherein L, Q, R₁, (R₂), R₄, V, W, and X are as defined above, and wherein R₂₀ is iodo or bromo;

(b) subjecting the product of step "a" to dehydrohalogenation with a tertiary amine to form the enol ether; and (c) separating the product.

In another process for the enol ether compounds, the formula-III and -IV halo compounds are subjected to dehydrohalogenation with a reagent selected from the group consisting of sodium or potassium superoxide, sodium or potassium carbonate, sodium or potassium hydroxide, sodium or potassium benzoate, sodium or potassium acetate, sodium or potassium trifluoroacetate, sodium or potassium bicarbonate, silver acetate, and a tetraalkylammonium superoxide of the formula $(R_{12})_4NO_2$ wherein $R_{12}$ is alkyl of one to 4 carbon atoms, inclusive to form the enol ethers.

Still another process for the enol ether compounds comprises the steps of starting with the (5Z) isomers represented by the formula

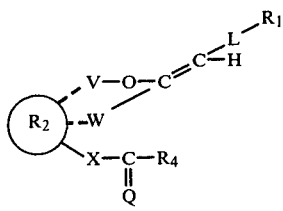

wherein L, Q, R₁, (R₂), R₄, V, W, and X are as defined above, and (a) isomerizing to an equilibrium mixture consisting of said starting compound and said enol ether product in a solution containing a catalytic amount of iodine, and (b) separating the components of that mixture.

The formula-III and -IV halo compounds obtained in the processes above are useful not only as intermediates for preparing the novel enol ethers but also for their pharmacological activity. A few of their biological responses are: inhibition of blood platelet aggregation, stimulation of smooth muscle, systemic blood pressure lowering, inhibiting gastric secretion and reducing undesirable gastrointestinal effects from systemic administration of prostaglandin synthetase inhibitors.

In addition to the iodo and bromo compounds of formula-III and -IV, the corresponding chloro and fluoro compounds are herein disclosed as useful compounds for the same purposes. They are included in general formulas corresponding to III and IV wherein $R_{20}$ is replaced with $R_{21}$ which includes iodo, bromo, chloro, and fluoro. The chloro and fluor compounds are readily prepared from the iodo or bromo compounds by methods known in the art, for example halide exchange in a solvent such as dimethylformamide. See for example Harrison et al., Compendium of Organic Synthetic Methods, Wiley-Interscience, N.Y., 1971, Section 145.

Reference to Chart A, herein, will make clear the steps for preparing the formula-I, -III, and -IV compounds of this invention.

In Chart A, the terms have the same meaning as defined above, namely:

(R₂) is

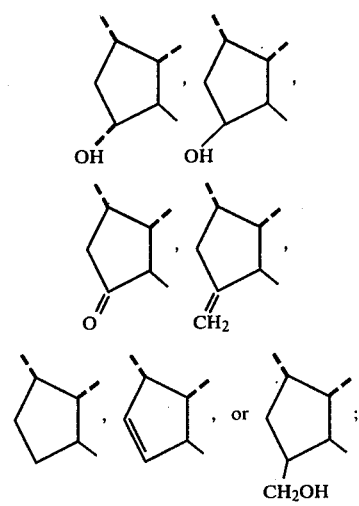

CHART A

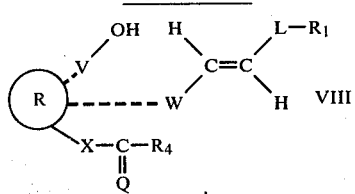

-continued
CHART A

[Structures III and IV shown, leading via (b) and (b') to Structure I]

Structure III: R₂ circle with V—O—C(H)(R₂₀)—C(H)—L—R₁, W, X—C(=Q)—R₄

Structure IV: (same as III with + charge indicated)

Structure I: R₂ circle with V—O—C=C(H)—L—R₁, W, X—C(=Q)—R₄

L is
(1) —(CH₂)$_d$—C(R₂₂)₂
(2) —CH₂—O—CH₂—Y— or
(3) —CH₂CH=CH— wherein d is zero to 5; R₂₂ is hydrogen, methyl, or fluoro, being the same or different with the proviso that one R₂₂ is not methyl when the other is fluoro; and Y is a valence bond or —(CH₂)$_k$—
wherein k is one or 2;

Q is $$\underset{O}{\overset{\parallel}{C}},\quad \overset{H}{\underset{H}{C}},\quad R_8\cdots OH,\quad \text{or}\quad R_8\cdots OH$$

wherein R₈ is hydrogen or alkyl of one to 4 carbon atoms, inclusive:

R₁ is
(1) —COOR₃
(2) —CH₂OH
(3) —CH₂N(R₉)₂
(4) —C(=O)—N(R₉)₂ or
(5) —C(NH—N=N—N)

wherein R₃ is (a) alkyl of one to 12 carbon atoms, inclusive, (b) cycloalkyl of 3 to 10 carbon atoms, inclusive, (c) aralkyl of 7 to 12 carbon atoms, inclusive, (d) phenyl, (e) phenyl substituted with one, 2, or 3 chloro or alkyl of one to 4 carbon atoms, inclusive;

(f) —C₆H₄—NH—C(=O)—C₆H₄—NH—C(=O)—CH₃, (g) —C₆H₄—NH—C(=O)—C₆H₅, (h) —C₆H₄—NH—C(=O)—CH₃, (i) —C₆H₄—NH—C(=O)—NH₂, (j) —C₆H₄—CH=N—NH—C(=O)—NH₂, (k) 2-naphthyl, (l) —CH(R₁₁)—C(=O)—R₁₀, wherein R₁₀ is phenyl, p-bromophenyl, p-biphenylyl, p-nitrophenyl, p-benzamidophenyl, or 2-naphthyl; and wherein R₁₁ is hydrogen or benzoyl; (m) hydrogen, or (n) a pharmacologically acceptable cation; and wherein R₉ is hydrogen or alkyl of one to 4 carbon atoms, inclusive, being the same or different;

R₄ is (1) —C(R₅)(R₆)—C$_g$H$_{2g}$—CH₃

(2) —C(R₅)(R₆)—Z—C₆H₄—(T)$_s$   or (3) —CH₂—C(H)=C(H)—CH₂CH₃ wherein C$_g$H$_{2g}$ is alkylene of one to 9 carbon atoms, inclusive, with one to 5 carbon atoms, inclusive, in the chain between —CR₅R₆— and terminal methyl, wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro and the further proviso that neither R₅ nor R₆ is fluoro when Z is oxa (—O—); wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between CR₅R₆— and the phenyl ring;

wherein T is alkyl of one to 4 carbon atoms, inclusive, fluoro, chloro, trifluoromethyl, or —OR₇— wherein R₇ is alkyl of one to 4 carbon atoms, inclusive, and s is zero, one, 2 or 3, with the proviso that not more than two T's are other than alkyl and when s is 2 or 3 the T's are either the same or different;

V is a valence bond or methylene;

W is —(CH₂)$_h$— wherein h is one or two; and

X is
(1) trans—CH=CH—
(2) cis—CH=CH—
(3) —C≡C— or
(4) —CH$_2$CH$_2$—

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof. Examples of cycloalkyl of 3 to 10 carbon atoms, inclusive, which includes alkyl-substituted cycloalkyl, are cyclopropyl,
2-methylcyclopropyl,
2,2-dimethylcyclopropyl,
2,3-diethylcyclopropyl,
2-butylcyclopropyl,
cyclobutyl,
2-methylcyclobutyl,
3-propylcyclobutyl,
2,3,4-triethylcyclobutyl,
cyclopentyl,
2,2-dimethylcyclopentyl,
3-pentylcyclopentyl,
3-tert-butylcyclopentyl,
cyclohexyl,
4-tert-butylcyclohexyl,
3-isopropylcyclohexyl,
2,2-dimethylcyclohexyl,
cyclopentyl,
cyclooctyl,
cyclononyl,
and cyclodecyl.

Examples of aralkyl of 7 to 12 carbon atoms, inclusive, are benzyl,
phenethyl,
1-phenylethyl,
2-phenylpropyl,
4-phenylbutyl,
3-phenylbutyl,
2-(1-naphthylethyl),
and 1-(2-naphthylmethyl).

Exampls of phenyl substituted by one to 3 chloro or alkyl of one to 4 carbon atoms, inclusive are p-chlorophenyl,
m-chlorophenyl,
o-chlorophenyl,
2,4-dichlorophenyl,
2,4,6-trichlorophenyl,
p-tolyl,
m-tolyl,
o-tolyl,
p-ethylphenyl,
p-tert-butylphenyl,
2,5-dimethylphenyl,
4-chloro-2-methylphenyl,
and 2,4-dichloro-3-methylphenyl.

Examples of alkylene of one to 9 carbon atoms, inclusive, with one to 5 carbon atoms, inclusive, in the chain, within the scope of $C_gH_{2g}$ as defined above, are methylene, ethylene, trimethylene, tetramethylene, and pentamethylene, and those alkylene with one or more alkyl substituents on one or more carbon atoms thereof, e.g. —CH(CH$_3$)—, —C(CH$_3$)$_2$—, —CH(CH$_2$CH$_3$)—, —CH$_2$—CH(CH$_3$)—, —CH(CH$_3$)—CH(CH$_3$)—, —CH$_2$—C(CH$_3$)$_2$—, —CH$_2$—CH(CH$_3$)—CH$_3$—, —CH$_2$—CH$_2$—CH(CH$_2$CH$_2$CH$_3$)—, —CH(CH$_3$)—CH(CH$_3$)—CH$_2$—CH$_2$—, —CH$_2$—CH$_2$—CH$_2$—C(CH$_3$)$_2$—CH$_2$, and —CH$_2$—CH$_2$—CH$_2$—CH$_2$—CH(CH$_3$)—. Examples of alkylene of one to 9 carbon atoms, inclusive, substituted with zero, one, or 2 fluoro atoms, inclusive, with one to 6 carbon atoms in the chain, within the scope of $C_jH_{2j}$ as defined above, are those given above for $C_gH_{2g}$ and hexamethylene, including hexamethylene with one of more alkyl substituents on one or more carbon atoms thereof, and including those alkylene groups with one or 2 fluoro substituents on one or 2 carbon atoms thereof, e.g. —CHF—CH$_2$—, —CHF—CHF—, —CH$_2$—CH$_2$—CF$_2$—, —CH$_2$—CHF—CH$_2$—, —CH$_2$—CH$_2$—CF(CH$_3$)—, —CH$_2$—CH$_2$—CF$_2$—CH$_2$—, —CH(CH$_3$)—CH$_2$—CH$_2$—CHF—, —CH$_2$—CH$_2$—CH$_2$—CH$_2$—CF$_2$—, —CHF—CH$_2$—CH$_2$—CH$_2$—CH$_2$—CHF—, —CF$_2$—CH$_2$—CH$_2$—CH$_2$—CH$_2$—CH$_2$—, —CH$_2$—CH$_2$—CH$_2$—CF$_2$—CH$_2$—CH$_2$—, and —CH$_2$—CH$_2$ —CH$_2$—CH$_2$—CH$_2$—CF$_2$.

Examples of

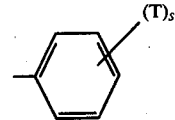

as defined above are phenyl,
(o-, m-, or p-)tolyl,
(o-, m-, or p-)ethylphenyl,
(o-, m-, or p-)propylphenyl,
(o-, m-, or p-)butylphenyl,
(o-, m-, or p-)isobutylphenyl,
(o-, m-, or p-)tert-butylphenyl,
2,3-xylyl,
2,6-diethylphenyl,
2-ethyl-p-tolyl,
4-ethyl-o-tolyl,
5-ethyl-m-tolyl,
2-propyl-(o-, m-, or p-)tolyl,
4-butyl-m-tolyl,
6-tert-butyl-m-tolyl,
4-isopropyl-2,6-xylyl,
3-propyl-4-ethylphenyl,
(2,3,4-, 2,3,5-, 2,3,6-, or 2,4,5-)trimethylphenyl,
(o-, m-, or p-)fluorophenyl,
2-fluoro-(o-, m-, or p-)tolyl,
4-fluoro-2,5-xylyl,
(2,4-, 2,5-, 2,6-, 3,4-, or 3,5-)difluorophenyl,
(o-, m-, or p-)chlorophenyl,
2-chloro-p-tolyl,
(3-, 4-, 5-, or 6-)chloro-o-tolyl,
4-chloro-2-propylphenyl,
2-isopropyl-4-chlorophenyl,
4-chloro-3,5-xylyl,
(2,3-, 2,4-, 2,5-, 2,6-, 3,4-, or 3,5-)dichlorophenyl,
4-chloro-3-fluorophenyl,
(3-, or 4-)chloro-2-fluorophenyl,
α,α,α-trifluoro-(o-, m-, or p-)tolyl,
(o-, m-, or p-)methoxyphenyl,
(o-, m-, or p-)ethoxyphenyl, (4- or 5-)chloro-2-methoxyphenyl, and 2,4-dichloro(5- or 6-)methoxyphenyl.

Referring to Chart A, the starting materials of formula VIII are known in the art or are readily available by processes known in the art. For example, as to 5,6-trans-PGF$_{2\alpha}$, see U.S. Pat. No. 3,759,978.

Other 5,6-trans-PGF$_{2\alpha}$ analogs and derivatives within the scope of Formula VIII are available from the corresponding PGF$_{2\alpha}$ compounds having the 5,6-cis configuration, for example by isomerization to an equilibrium mixture containing the 5,6-trans isomer by ultraviolet radiation in the presence of a diaryl sulfide or disulfide. See above cited U.S. Pat. No. 3,759,978.

For typical PGF$_{2\alpha}$-type compounds useful as sources of the Formula-VIII 5,6-trans compounds, reference is made as follows: as to 15-methyl- and 15-ethyl-PGF$_{2\alpha}$, see U.S. Pat. No. 3,728,382; as to 16,16-dimethyl-PGF$_{2\alpha}$, see U.S. Pat. No. 3,903,131; as to 16,16-difluoro-PGF$_{2\alpha}$ compounds, see U.S. Pat. No. 3,962,293 and 3,969,380; as to 16-phenoxy-17,18,19,20-tetranor-PGF$_{2\alpha}$, see Derwent Farmdoc No. 73279U and British Spec. No. 1,409,841; as to 17-phenyl-18,19,20-trinor-PGF$_{2\alpha}$, see U.S. Pat. No. 3,987,087; as to 11-deoxy-PGF$_{2\alpha}$, see Derwent Farmdoc No. 10695V and British Spec. No. 1,434,620; as to PGD$_2$, see U.S. Pat. No. 3,767,813; as to 2a, 2b -dihomo-PGF$_{2\alpha}$, see Derwent Farmdoc No. 61412S and U.S. Pat. No. 3,852,316 and 3,974,195; as to 3-oxo-PGF$_{2\alpha}$, see U.S. Pat. No.3,923,861; as to 3-oxa-17-phenyl-18,19,20-trinor-PGF$_{2\alpha}$, see U.S. Pat. No. 3,931,289; as to substituted phenacyl esters, see Derwent Farmdoc No. 16828X and German Offen. 2,535,693; as to substituted phenyl esters, see U.S. Pat. No. 3,890,372; as to C-1 alcohols, i.e. 2-decarboxy-2-hydroxymethyl compounds, see U.S. Pat. No. 3,636,120; as to C-2 tetrazolyl derivatives, see U.S. Pat. No. 3,883,513 and 3,932,389; as to $\Delta$2-PGF$_{2\alpha}$-see Derwent farmdoc No. 46497W and Ger. Offen. 2,460,285; as to 2,2-dimethyl-PGF$_{2\alpha}$ analogs, see Derwent Farmdoc No. 59033T and Ger. Offen. 2,209,039; as to 9-deoxy-9-hydroxy-methyl-PGF$_{2\alpha}$, see U.S. Pat. No. 3,950,363; as to 11$\beta$-PGF$_{2\alpha}$ compounds, see U.S. Pat. No. 3,890,371; as to 11-deoxy-11-hydroxymethyl-PGF$_{2\alpha}$, see U.S. Pat. Nos. 3,931,282 and 3,950,363; as to 16-methylene-PGF$_{2\alpha}$, see Derwent Farmdoc No. 19594W and U.S. Pat. No. 3,953,495; as to 17,18-didehydro-PGF$_{2\alpha}$ compounds, see U.S. Pat. No. 3,920,726; as to 3-(or 4-)oxa-17,18-didehydro-PGF$_{2\alpha}$ -compounds, see U.S. Pat. 3,920,723; as to 15-oxo-PGF$_{2\alpha}$, see U.S. Pat. No. 3,728,382; as to 15-deoxy-PGF$_{2\alpha}$, see Derwent Farmdoc No. 9239W; as to 13,14-cis compounds, see U.S. Pat. No. 3,932,479; as to 11-deoxy-15-deoxy-PGF$_{2\alpha}$ see Derwent Farmdoc No. 5694U and U.S. Pat. No. 3,853,951; as to $\omega$-homo-PGF$_{2\alpha}$ compounds, see Derwent Farmdoc No. 4728W; and as to 2,2-difluoro-PGF$_{2\alpha}$ compounds, see U.S. Pat. No. 4,001,300.

As to 2-decarboxy-2-amino-PGF$_{2\alpha}$ compounds, see the Appendix attached hereto, with a disclosure taken from a prior-filed, commonly-owned U.S. Pat. application.

In step "a" of Chart A, the starting material VIII is subjected to iodination and cyclization to yield the formula-III and -IV iodo compounds. For this purpose there is used either an aqueous system containing iodine, potassium iodide, and an alkali carbonate or bicarbonate, or an organic solvent system such as methylene chloride containing iodide in the presence of an alkali metal carbonate. The reaction is carried out at temperatures below 25° C., preferably about 0°–5° C. for 1–20 hr. Thereafter the reaction is quenched with sodium sulfite and sodium carbonate and the formula-III and -IV compounds separated from the reaction mixture.

The formula-III and -IV compunds wherein R$_{20}$ is bromo are conveniently prepared using N-bromosuccinimide in a solvent such as methylene chloride at temperatures between 0° C. and 30° C.

The formula-III and -IV compounds, which are isomeric at C-5 and C-6, are separated by conventional methods of fractionation, column chromatography, or liquid-liquid extraction. Especially useful is high pressure liquid chromatography on silica gel. The less polar compound is identified as the Formula-iv (5R,6S) isomer and the more polar comound as the Formula-III (5S,6R) isomer.

In steps "b" and "b'", either isomer of the halo ether us converted to the desired Formula-I product. Accordingly, a mixture of those halo ether isomers will likewise yield a Formula-I product.

The halo compound III or IV is converted to the formula-I enol ether by contacting it with a dehydroiodination reagent. For such reagents see, for example, Fieser and Fieser, "Reagents for Organic Synthesis" p.1308, John Wiley and Sons, Inc., New York, N.Y. (1967). Preferred for the reaction are tertiary amines and reagents selected from the group consisting of sodium or potassium superoxide, sodium or potassium carbonate, sodium or potassium hydroxide, sodium or potassium benzoate, sodium or potassium acetate, sodium or potassium trifluoroacetate, sodium or potassium bicarbonate, silver acetate, and a tetraalkylammonium superoxide of the formula (R$_{12}$)$_4$NO$_2$ wherein R$_{12}$ is alkyl of one to 4 carbon atoms, inclusive Of the tertiary amines, preferred amines are 1,5-diazabicyclo [4.3.0] nonene-5("DBN"),
1,4-diazabicyclo [2.2.2] octane ("DABCO"), and
1,5-diazabicyclo [5.4.0 undecene-5 ("BDU").

Other preferred reagents are sodium or potassium superoxide and tetramethylammonium superoxide. For further information on the superoxides see Johnson and Nidy, J. Org. Chem. 40, 1680 (1975). For larger scale preparation the electrochemical generation of superoxide is recommended. See Dietz et al., J. Chem. Soc. (B), 1970, pp. 816–820.

The dehydroiodination step is carried out in an inert organic medium such as dimethylformamide and is followed by TLC to show the disappearance of starting material. The reaction proceeds at 25° C. and can be accelerated at 40°–50° C.

In working up the reaction mixture it is advantageous to maintain basic conditions, e.g. with triethylamine, to avoid acidic decomposition or structural changes of the product. Purification is achieved by crystallization and consequent separation from impurities or starting material left in the mother liquor, or by column chromatography. For chromatographic separation a column of magnesium silicate ("Fluorisol ®") is preferred over silica gel. Decomposition of the product is avoided by pretreating the column with triethylamine.

Ester groups such as the p-phenylphenacyl group on the C-1 carboxyl or 4-bromobenzoate on C-11 and C-15 hydroxyls are unchanged by the transformations of Chart A, and, if present on the formula-VIII starting mterial, are also present on the formula-I product. For the final products of formula I which are esters the peferred method of preparation is from formula-I, -III or -IV halo compounds which are corresponding esters.

Esters may also be prepared from the corresponding acids of formula I, III, and IV, i.e., wherein $R_1$ is —COOH, by methods known in the art. For example, the alkyl, cycloalkyl, and aralyl esters are prepared by interaction of said acids with the appropriate diazohydrocarbon. For example, when diazomethane is used, the methyl ester are produced. Similar use of diazoethane, diazobutane, 1-diazo-2-ethylhexane, diazocyclohexane, and phenyldiazomethane, for example, gives the ethyl, butyl, 2-ethylhexyl, cyclohexyl, and benzyl esters, respectively. Of these esters, the methyl or ethyl are preferred.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example Organic Reactions, John Wiley and Sons, Inc., New York, N.Y., Vol. 8, pp. 389-394 (1954).

The formula I, III and IV compounds prepared by the processes of this invention are transformed to lower alkanoates by interaction with a carboxyacylating agent, preferably the anhydride of a lower alkanoic acid, i.e., an alkanoic acid of one to 8 carbon atoms, inclusive. For example, use of acetic anhydride gives the corresponding diacetate. Similar use of propionic anhydride, isobutyric anhydride, and hexanoic acid anhydride gives the corresponding carboxyacylates.

The carboxyacylation is advantageously carried out by mixing the hydroxy compound and the acid anhydride, preferably in the presence of a tertiary amine such as pyridine or triethylamine. A substantial excess of the anhydride is used, preferably about 10 to about 1,000 moles of ahydride per mole of the hydroxy compound reactant. The excess anhydride serves as a reaction diluent and solvent. An inert organic diluent, for example dioxane, can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° To about 100° C. The necessary reaction time will depend on such factors as the reaction temperature, and the nature of the anhydride; pyridine, and a 25° C. reaction temperature, a 12 to 24-hour reaction time is used.

The carboyacylated product is isolated from the reaction mixture by conventional methods. For example, the excess anhydride is decomposed with water, and thw resulting mixture acidified and then extracted with a solvent such as diethyl ether. The desired carboxylate is recovered from the diethyl ether extract by evaporation. The carboxylate is then purified by conventional methods, advantageously by chromatography.

Salts of these formula-I, -III and -IV compounds are prepared with pharmacologically acceptable metal cations, ammonium, amine cations, or quaternary ammonium cations. Several methods are employed, for example using either the formula-VIII starting materials in their salt form or, when considered as intermediates in preparing the formula-I products; the formula-III or -IV compounds in their salt form. In addition, the free acids may be prepared by careful acidification of a soluble alkali metal salt of a formula I, III or IV compound and extraction into an organic solvent to avoid prolonged contact with an acidic aqueous medium, thereupon the desired salt may be prepared from the stoichiometric amount of hydroxide, carbonate, or bicarbonate in the case of metal cations, of the amine or hydroxide in the case of other salts.

Especially useful for administration because of their ease of dissolving are sodium salts. They are obtained from the formula-I, -III, or -IV esters by saponification with equivalent amounts of sodium hydroxide in a solvent, preferably an alcohol-water solution, thereafter lyophilizing (freeze-drying) the mixture to obtain the powdered product. The starting esters are preferably alkyl esters, of which methyl or ethyl are especially preferred.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitble amines are methylamine, dimethylamine, trimethylamine, etylamine, dibutylamine, triisopropylamine, N-methylhexylamine, decylamine, dedecylamine, allylaine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 atoms, as well as heterocyclic amines, e.g., piperidine, morphiline, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amine-2-methyl-1-propanol, tris(hydroxymethyl)aminomethane, N-phenylethanolamine, N-(p-tert-amylphenyl)diethanolamine, galactamine, N-methyl-glucamine, N-methylglycosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

As discussed above, the compounds of formula I, III, and IV are administered in various ways for various purposes; e.g., intravenously, intramuscularly, subcutaneously, orally, intravaginally, rectally, buccally, sublingually, topically, and in the form of sterile implants for prolonged action.

For intravenous injection or infusion, sterile aqueous isotonic solutions are preferred. For that purpose, it is preferred because of increased water solubility that $R_3$ in the formula I, III, and IV compounds be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral sublingual administration. For rectal or vaginal administration suppositories prepared as known in the art are used. For tissue implants, a sterile tablet or silicone rubber capsule or other object containing or imprenated with the substance is used.

In Chart B, is shown a process for preparing 6-keto-PGF$_{1\alpha}$ compounds. These compounds, not the subject of this invention, are known to have pharmocological utility including inhibition of blood platelet aggregation, stimulation of smooth muscle, and systemic blood pressure lowering. The formula-1 enol ethers are converted to the formula-IX compounds by contact with an aqueous acid, preferably

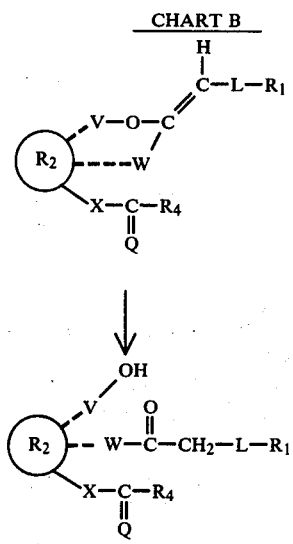

in an organic solvent. Examples of suitable acids are dilute hydrochloric, perchloric, and sulfuric acids.

In Chart C are shown process steps yielding the formula-III halo ethers in the formula-XII amide form, useful per se or as starting materials for formula-I amides by step "b" of Chart A.

In step "a" of Chart C of the formula-X ester is saponified and acidified to form the formula-XI free acid. The conditions and reagents are those employed in similar transformations known in the art.

In step "b" the formula-XII amide is formed from acid XI, for example by contact with either ammonia or amine in the presence of isobutylchloroformate, preferably in a solvent such as acetonitrile.

In Chart D is shown the equilibration of the formula-I and formula-XIII compounds, starting with either one and yielding a mixture consisting of the two compounds. The reaction goes smoothly in the presence of a catalytic amount(0.1–2.0 mg.) of iodine and is preferably run in a solvent containing a trace (0.1%) of a tertiary amine such as triethylamine. Thereafter the mixture is separated into its components, for example by preparative thin layer chromatography. The formula-XIII compounds are known to be useful for pharmological purposes. One of the formula-XIII compounds is designated by the term "prostacyclin".

It should be understood that although the Charts have formulas drawn with a specific configuration for the reactants and products, the procedural steps are intended to apply also to mixtures, including racemic mixtures or mixtures of enantiomeric forms. Accordingly, it is intended that the compounds are claimed not only in their purified form but also in mixtures, including racemic mixtures or mixtures of the enantiomeric forms.

CHART C

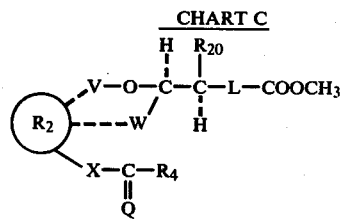

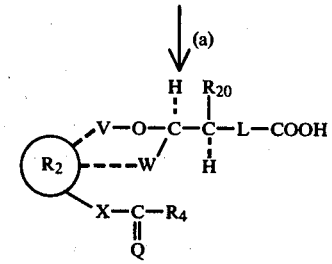

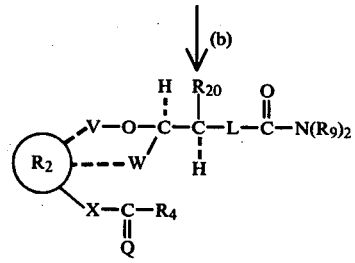

CHART D

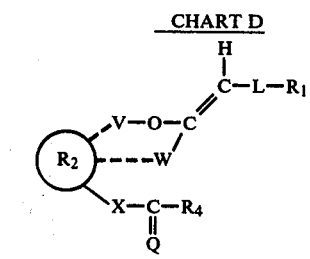

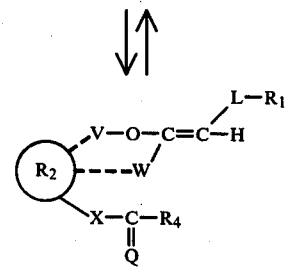

If optically active products are desired, optically active starting materials or intermediates are employed or, if racemic starting materials or intermediates are used, the products are resolved by methods known in the art for prostaglandins. The products formed from each step of the reaction are often mixtures and, as known to one skilled in the art, may be used as such for a succeeding step or, optionally separated by conventional methods of fractionation, column chromatography, liquid-liquid extraction, and the like, before proceeding.

To obtain the optimum combination of biological response specificity, potency, and duration of activity, certain compounds within the scope of formulas I-IV are preferred. For example it is preferred that Q be

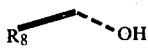

wherein it is especially preferred that $R_8$ be hydrogen or methyl.

Another preference, for the compounds of formulas I, III, and IV as to $R_1$, is that $R_3$ in —COOR$_3$ be either hydrogen or alkyl of one to 12 carbon atoms, inclusive. it is further preferred that $R_3$ be alkyl of one to 4 carbon atoms, inclusive, especially methyl or ethyl, for optimum absorption on administration. For the compounds of formula-II, it is preferred that $R_3$ not be hydrogen but rather an alkyl ester or a salt of pharmologically acceptable cation.

For purposes of stability on long storage, it is also preferred that $R_3$ be amido-substituted phenyl or substituted phenacyl, as illustrated herein.

For oral administration it is preferred that $R_1$ be

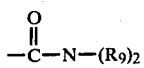

and that $R_9$ be hydrogen or methyl.

When $R_4$ is

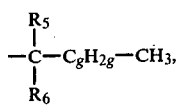

it is preferred that $C_gH_{2g}$ be alkylene of 2, 3, or 4 carbon atoms, and especially that it be trimethylene. It is further preferred that $R_5$ and $R_6$ be hydrogen, methyl, ethyl, or fluoro, being the same or different. It is further preferred, when $R_5$ and $R_6$ are not hydrogen, that both $R_5$ and $R_6$ be methyl for fluoro.

When $R_4$ is

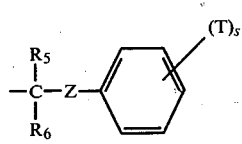

it is preferred that "s" be either zero or one. When "s" is not zero, it is preferred that T be methyl, chloro, fluoro, trifluoromethyl, or methoxy with meta or para attachement to the phenyl ring. When Z is oxa (—O—), it is preferred that $R_5$ and $R_6$ be hydrogen, methyl, or ethyl, being the same or different. It is further preferred, when $R_5$ and $R_6$ are not hydrogen, that both $R_5$ and $R_6$ be methyl. When Z is $C_jH_{2j}$, it is preferred that $C_jH_{2j}$ be a valence bond, methylene, or ethylene.

As to variations in (R$_2$), it is preferred that (R$_2$) be

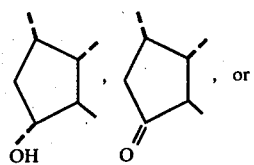

As to variations in $R_4$, it is preferred that $R_4$ be n-pentyl 1,1-dimethylpentyl 1,1-difluoropentyl

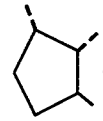

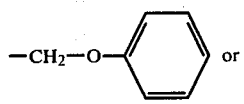

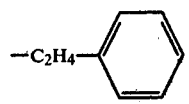

As to variations in L it is preferred that L be —(CH$_2$)$_3$—, —(CH$_2$)$_4$—, or —(CH$_2$)$_5$—, especially —(CH$_2$)$_3$—.

BRIEF DESCRIPTION OF THE DRAWING

The FIGURE, attached herewith, depicts the proton ($^1$H) nuclear magnetic resonance (NMR) spectrum of one of the formula-I compounds described herein, namely (5E)-9-Deoxy-6,9α-epoxy-Δ$^5$-PGF$_1$, methyl ester. Significant peaks are at 5.53, 4.67, 4.52, 4.02, 3.83, and 3.678.

DESCRIPTION OF THE PREFERRED EMBODIMENTS

The invention is further illustrated, but not limited to, the following examples.

All temperatures are in degrees centigrade.

Infrared absorption spectra are recorded on a Perkin-Elmer model 421 infrared spectrophotometer. Except when specified otherwise, undiluted (neat) samples are used.

The NMR spectra are recorded on a Varian A-60, A-60D, T-60 or XL-100 spectrophotometer is deuterochloroform solutions with tetramethylsilane as an internal standard.

Mass spectra are recorded on a Varian Model MAT CH7 Mass Spectrometer, a CEC Model 110B Double Focusing High Resolution Mass Spectrometer, or an LKB Model 9000 Gas Chromatograph-Mass Spectrometer (ionization voltage 22 or 70 ev.).

"Brine", herein refers to an aqueous saturated sodium chloride solution.

"DBN", herein, refers to 1,5-diazabicyclo[4.3.0]nonene-5.

"DABCO", herein refers to 1,4-diazabicyco[2.2.2]octane.

"DBU", herein, refers to 1,5-diazabicyclo[5.4.0]undecene-5.

"E" and "Z", herein, follow Blackwood et al., cited above.

"Florisil ®", herein, is a chromatographic magnesium silicate produced by the Floridin Co. See Fieser et al. "Reagents for Organic Synthesis" p. 393 John Wiley and Sons, Inc., New York, N.Y. (1967).

"TLC", herein, refers to thin layer chromatography.

Silica gel chromatography, as used herein, is understood to include elution, collection of fractions, and combinations of those fractions shown by TLC to contain the desired product free of starting material and impurities.

"Concentrating", as used herein, refers to concentration under reduced pressure, preferably at less than 50 mm. and at temperatures below 35° C.

"Dicyclohexyl-18-crown-6", herein, refers to a compound reported by C. J. Pedersen, J. Am. Chem. Soc. 89, 7017 (1967)).

"Lower alkanoate", herein, refers to an ester of an alkanoic acid of one to 8 carbon atoms, inclusive.

Preparation 1

(5R,6R)-5-Iodo-9-deoxy-6,9α-epoxy-PGF$_1$, Methyl Ester and (5S,6S)-5-Iodo-9-deoxy-6,9α-epoxy-PGF$_1$, Methyl Ester.

A suspension of PGF$_{2\alpha}$, methyl ester (3.0 g.) in 60 ml. of water is treated with sodium carbonate (1.7 g.) and cooled in an ice bath. To the resulting solution is added potassium iodide (2.7 g.) and iodine (4.14 g.) and stirring continued for 3 hr. at about 0° C. Thereafter sodium sulfite (2.5 g.) and sodium carbonate (0.8 g.) are added to decolorize the mixture. After a few minutes the mixture is extracted with chloroform. The organic phase is washed with brine, dried over sodium sulfate, and concentrated to yield mainly the title compound, an oil, which is further purified by silica gel chromatography, eluting with methylene chloride (15–50%)-acetone to yield the less polar (5S, 6S) tital compound, 0.29 g. and the more polar (5R, 6R) title compound, 3.36 g.

Preparation 2

(5Z)-9-Deoxy-6,9α-epoxy-Δ$^5$-PGF$_1$, Methyl Ester (Formula XIII, Chart D: $(R_2)$ is

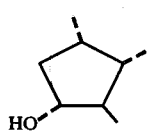

L is —(CH$_2$)$_3$—, Q is

R$_1$ is —COOCH$_3$, R$_4$ is n-pentyl, V is a valence bond, W is methylene, and X is trans—CH=CH—).

A mixture of potassium superoxide (0.427 g.). dicyclohexyl-18-crown-6 (0.75 g.) and 10 ml.) of dimethyformamide is stirred at about 25° C. for 0.25 hr. A solution of (5R, 6R)-5-iodo-9-deoxy-6,9α-epoxy-PGF$_1$, methyl ester (Preparation 1, 0.494 g.) in 1 ml. of dimethylformamide is then added, while stirring. After 5 min. the reaction mixture is quenched in ice-water and extracted with diethyl eter. The organic phase is dried and concentrated. The residue is subjected to column chromatography on Florisil ® pretreated with treithylamine (5%)-methylene chloride. The product is eluted with ethyl acetate-hexane-triethylamine (50:50:0.1) to give the formula-XIII title compound, 0.152 g., having R$_f$0.69 (TLC on silica gel in acetone-hexane (1:1), and having proton NMR peaks at 5.54, 4.58, 4.16, 4.00, 3.75, 3.65, and 0.87 δ.

EXAMPLE 1

(5S,6R)-5-Iodo-9-dexoy-6,9α-epoxy-PGF$_1$, Methyl Ester Formula III: $(R_2)$ is

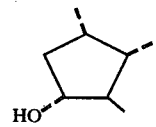

L is —(CH$_2$)$_3$—, Q is

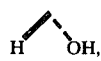

R$_1$ is —COOCH$_3$, R$_4$ is n-pentyl, R$_{20}$ is iodo, V is a valence bond, W is methylene, and X is trans—CH=CH—) and (5R,6S)-5Iodo-9-deoxy-6,9α-epoxy-PGF$_1$, Methyl Ester (Formula IV: wherein L, Q, R$_1$, R$_2$, R$_4$, R$_{20}$, V, W, and X are as above).

Refer to Chart A. A solution of the formula-VIII 5,6-trans-PGF$_{2\alpha}$, methyl ester (U.S. Pat. No. 3,823,180, 2.58 g.) in 50 ml. of methylene chloride is treated, while ice-cold, with sodium carbonate (1.48 g.) and iodine (1.90 g.) for one hr., thereafter at about 25° C. for another hr. The mixture is poured into 100 ml. of ice-water containing sufficient excess sodium thiosulfate to decolorize the mixture. The organic phase is separated and later combined with chloroform extracts of the aqueous phase, dried over magnesium sulfate, and concentrated. The residue (3.48 g.) is subjected to high pressure liquid chromatography on silica gel, eluting with acetone (15–25%)-methylene chloride (and again chromatographing the fraction containing a mixture of products) to give the less polar Formula-IV (5R,6S) title compound, 0.352 g., having proton NMR peaks at 5.55, 3.5–4.5, 3.67, and 0.90 δ; mass spectral peaks (TMS derivative) at 638.2327, 623, 607, 567, 548, 517, 511, 510, 477, 451, 199, and 173; and R$_f$0.42 (TLC on silica gel in acetone (20%)-methylene chloride); and the more polar Formula-III (5S,6R) title compound, 2.151 g., having proton NMR peaks at 5.57, 4.52, 3.6–4.3, 3.70, and 0.92δ; mass spectral peaks (TMS derivative) at 638.2333, 623, 607, 567, 548, 517, 511, 510, 477, 451, 199, and 173; and R$_f$ 0.36 (TLC on silica gel in acetone (20%)-methylene chloride).

Following the procedures of Example 1, but replacing the formula-VIII starting material with the following formula-VIII compounds or their derivatives within the scope of R$_1$:

5,6-Trans-15-methyl-PGF$_{2\alpha}$
5,6-Trans-15-ethyl-PGF$_{2\alpha}$
5,6-Trans-16,16-dimethyl-PGG$_{2\alpha}$
5,6-Trans-16,16-difluoro-PGF$_{2\alpha}$
5,6-Trans-16-phenoxy-17,18,19,20-tetranor-PGF$_{2\alpha}$
5,6-Trans-17-phenyl-18,19,20-trinor-PGF$_{2\alpha}$
5,6-Trans-11-deoxy-PGF$_{2\alpha}$
2a,2b-Dihomo-5,6-trans-PGF$_{2\alpha}$
3-Oxa-5,6-trans-17-phenyl-18,19,20-trinor-PGF$_{2\alpha}$ there are obtained the corresponding formula-III and -IV iodo compounds.

EXAMPLE 2

(5E)-9-Deoxy-6,9α-epoxy-Δ⁵-PGF₁, Methyl Ester (Formula I: 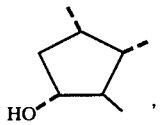 is

L is —(CH₂)₃—, Q is

H̸  ̸OH,

R₁ is —COOCH₃, R₄ is n-pentyl, V is a valence bond, W is methylene, and X is trans—CH=CH—).

Refer to Chart A. A mixture of potassium superoxide (0.88 g.), dicyclohexyl-18-crown-6 (cf. C. J. Pedersen, J. Am. Chem. Soc. 89, 7017 (1967)) and 20 ml. of dimethylformamide is stirred, first at about 25° C. for 0.5 hr., then at ice temperature while adding a solution of formula-III (5S,6R)-5-iodo-9-deoxy-6,9α-epoxy-PGF₁, methyl ester (Example 1, 1.74 g.) in 3 ml. of dimethylformamide. After 0.5 hr., the reaction mixture is poured into ice-water and extracted with diethyl ether. The organic phase is dried and concentrated to a residue, taken up in dimethylformamide and treated with additional potassium superoxide (approximately 0.26 g.) in 6 ml. of dimethylformamide at about 25° C. for 10 min. The residue obtained as above is subjected to column chromatography on Florisil ® pretreated with triethylamine (5%)-methylene chloride. The product is eluted with ethyl acetate-hexane-triethylamine (50:50:0.1) to give the formula-I title compound, 0.258 g., having m.p. 66°–69° C.; R$_f$0.65 (TLC on silica gel in acetone-hexane (1:1)); having proton NMR peaks at 5.53, 4.67, 4.52, 4.02, 3.83, 3.67, and 0.88 δ; having ¹³C NMR peaks at 174.3, 155.9, 136.4, 131.3, 95.9, 83.0, 77.3, 72.9, 55.5, 51.4, 45.6, 40.4, 37.2, 33.4, 31.7, 30.5, 26.9, 25.7, 25.2, 22.6, and 14.0 ppm. relative to tetramethylsilane; and having infrared absorption at 3420, 1740, and 1690 cm⁻¹. For more detail of the proton NMR spectrum see the FIGURE attached hereto. On the basis of that spectrum the structure and name are assigned.

Following the procedure of Example 2, but replacing potassium superoxide with each of the following reagents, the title compound is likewise obtained:

sodium superoxide
tetramethylammonium superoxide
sodium carbonate
potassium carbonate
sodium hydroxide
potassium hydroxide
sodium benzoate
potassium benzoate
sodium acetate
potassium acetate
sodium trifluoroacetate
potassium trifluoroacetate
sodium bicarbonate
potassium bicarbonate and
silver acetate.

EXAMPLE 3

(5E)-9-Deoxy-6,9α-epoxy-Δ⁵-PGF₁, Methyl Ester (Formula I: as defined in Example 2).

Refer to Chart A. A mixture of the formula-III (5S,6R)-5-iodo-9-deoxy-6,9α-epoxy-PGF₁, methyl ester (Example 1, 1.0 g.), 1.0 ml. of 1,5diazabicyclo[4.3.0]-nonene-5-("DBN") and 60 ml. of benzene is heated at about 42° C. for 20 hr. Thereupon 0.5 ml. of DBN is added and the heating continued for 6 hr. more. The mixture is left stirring at about 25° C. for 60 hr., then heated again for 8 hr. at 40°–50° C. The reaction mixture is cooled, washed with ice water mixed with a few drops of triethylamine, dried over magnesium sulfate, and concentrated. The residue is subjected to column chromatography as described in Example 2 to yield the title compound having the properties set forth in Example 2.

Following the procedure of Example 3 but replacing DBN of that example with 1,4-diazobicyclo[2.2.2]octane ("DABCO") or 1,5-diazabicyclo[5.4.0]undecene-5 ("DBU") there is obtained the same formula-I product.

Following the procedures of Examples 2 and 3, but replacing the formula-III iodo compound therein with each of the formula-III iodo compounds described following Example 1 there are obtained the corresponding formula-I compounds, including the derivatives within the scope of R₁. Thus there are obtained, for example, analogs of (5E)-9-deoxy-6,9α-epoxy-Δ⁵-PGF₁, methyl ester, having the following structural features:

15-methyl-,
15-ethyl-,
16,16-dimethyl-,
16,16-difluoro-,
16-phenoxy-17,18,19,20-,
17-phenyl-18,19,20-,
11-deoxy-,
2a,2b-dihomo-, and
3-oxa-17-phenyl-18,19,20-trinor-.

EXAMPLE 4

(5E)-9-Deoxy-6,9α-epoxy-Δ⁵-PGF₁, Sodium Salt (Formula I: 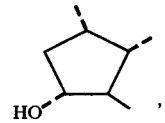 is

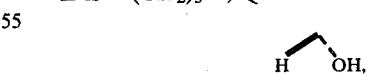

L is —(CH₂)₃—, Q is

H̸  ̸OH,

R₁ is —COONa, R₄ is n-pentyl, V is a valence bond, W is methylene, and X is trans—CH=CH—).

A solution of the formula-I (5E)-9-deoxy-6,9α-epoxy-Δ⁵-PGF₁, methyl ester (Example 2, 0.041 g.) in 5 ml. of methanol is treated with a solution of 2.5 ml. of 0.05 N. sodium hydroxide in 2.5 ml. of water at about 25° C. for 20 hr. The solution shown by TLC (1:1 acetone-hexane) to be free of starting material, is frozen at about −75° C. and lyophilized to yield the formula-I title compound as a viscous gum.

EXAMPLE 5

(5E)-9-Deoxy-6,9α-epoxy-Δ⁵-PGF₁ (Formula I: $R_2$ is

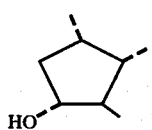

L is —(CH₂)₃—, Q is

$R_1$ is —COOH, $R_4$ is n-pentyl, V is a valence bond, W is methylene, and X is trans—CH=CH—).

A solution of the formula-I (5E)-9-deoxy-6,9α-epoxy-Δ⁵-PGF₁, sodium salt (Example 4, 0.10 g.) in 5 ml. of water is treated with a solution of 1 N. potassium hydrogen sulfate in water at ice bath temperature for 1 minute. The solution is immediately thereafter extracted with diethyl ether. The organic phase is dried and concentrated to yield the formula-I title compound.

EXAMPLE 6

6-Keto-PGF₁α, Methyl Ester (Formula IX: $R_2$ is

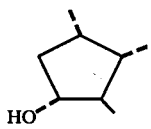

L is —(CH₂)₃—, Q is

$R_1$ is —COOCH₃, $R_4$ is n-pentyl, V is a valence bond, W is methylene and X is trans—CH=CH—).

Refer to Chart B. A solution of the formula-I (5E)-9-deoxy-6,9α-epoxy-Δ⁵-PGF₁, methyl ester (Example 2 0.096 g.) in 10 ml. of tetrahydrofuran containing 25 ml. of 0.2 M potassium chloride and 6.5 ml. of 0.2 M hydrochloric acid is stirred at about 25° C. for 1.5 hr. Thereafter 10 ml. of brine is added and the mixture extracted with ethyl acetate. The organic phase is dried and concentrated. The residue (0.088 g.) is subjected to high pressure liquid chromatography on silica gel, eluting with acetone (30%)-hexane, to yield the formula-IX title compound, 0.031 g., having m.p. 70°-74° C.

EXAMPLE 7

(5S,6R)-5-Bromo-9-deoxy-6,9α-epoxy-PGF₁, Methyl Ester Formula III: $R_2$ is

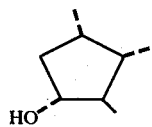

L is —(CH₂)₃—, Q is

$R_1$ is —COOCH₃, $R_4$ is n-pentyl, $R_{20}$ is bromo, V is a valence bond, W is methylene, and X is trans—CH=CH—); and (5R,6S)-5-Bromo-9-deoxy-6,9α-epoxy-PGF₁, Methyl Ester (Formula-IV: wherein $R_2$, L, Q, $R_1$, $R_4$, $R_{20}$, V, W, and X are as defined above).

Refer to Chart A. A solution of the formula-VIII 5,6-trans-PGF₂α, methyl ester, (U.S. Pat. No. 3,823,180, 3.68 g.) in 50 ml. of methylene chloride is treated, while ice-cold, with N-bromosuccinimide (1.78 g.) for one hr., thereafter at about 25° C. for another hr. The mixture is poured into 100 ml. of water containing sodium chloride. The organic phase is separated and later combined with methylene chloride extracts of the aqueous phase, dried over magnesium sulfate, and concentrated. The residue (4.2 g.) is subjected to chromatography on silica gel, eluting with ethyl acetate (50–75%)-hexane and with ethyl acetate to give the less polar Formula-IV 5R,6S, title compound and the more polar Formula-III 5S,6R title compound.

EXAMPLE 8

(5S,6R)-5-Iodo-9-deoxy-6,9α-epoxy-PGF₁ (Formula III: $R_2$ is

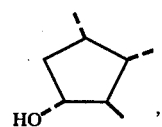

L is —(CH₂)₃—, Q is

$R_1$ is —COOH, $R_4$ is n-pentyl, $R_{20}$ is iodo, V is a valence bond, W is methylene, and X is trans—CH=CH—).

A solution of the formula-III methyl ester (Example 1, 1.0 g.) in 30 ml. of methanol is treated with 20 ml. of 3 N aqueous potassium hydroxide at about 0° C. for about 5 min., then at about 25° C. for 2 hr. The mixture is acidified with 45 ml. of 2 N potassium acid sulfate and 50 ml. of water to pH 1.0, saturated with sodium chloride and extracted with ethyl acetate. The organic phase is washed with brine, dried over sodium sulfate and concentrated to an oil, 1.3 g. The oil is subjected to silica gel chromatography, eluting with acetone-dichloromethane (30:70 to 50:50) to yield the formula-III acid title compound.

EXAMPLE 9

(5E)-9-Deoxy-6,9α-epoxy-Δ⁵-PGF₁, Amide (Formula I: $R_2$ is

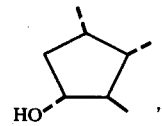

L is —(CH₂)₃—, Q is

$R_1$ is

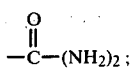

R$_4$ is n-pentyl, V is a valence bond, W is methylene, and X is trans—CH=CH—).

1. There is first prepared the formula-III (5S,6R)-5-iodo-9-deoxy-6,9α-epoxy-PGF$_1$, amide. A solution of the formula-III 5S,6R)-5-iodo-9-deoxy-6,9α-epoxy-PGF$_1$acid compound (Example 8, 0.50 g.) in 10 ml. of dry acetone is treated at −10° C. while stirring, with 0.3 ml. of triethylamine and 0.3 ml. of isobutylchloroformate. After 5 min. there is added a saturated solution of ammonia in acetonitrile, thereafter continuing the reaction at about 25° C. for 10 min. The mixture is filtered and the filtrate concentrated to an oil. The residue is taken up in ethyl acetate, washed with water, dried over magnesium sulfate, and concentrated. The residue is subjected to silica gel chromatography, eluting with acetone (40–100%)-methylene chloride to yield the desired amide.

II. The title compound is next prepared. Following the procedure of Example 2, but replacing the (5S,6R)-5-iodo-9-deoxy-6,9α-epoxy-PGF$_1$-methyl ester starting material of that example with the product of Part I above, there is obtained the formula-I title compound.

III. Likewise, following the procedure of Example 3 but replacing the 5S,6R)-5-iodo-9-deoxy-6,9α-epoxy-PGF$_1$, methyl ester starting material of that example with the product of Part I above, there is also obtained the formula-I title compound.

EXAMPLE 10

(5E)-9-Deoxy-6,9α-epoxy-Δ$^5$-PGF$_1$, Methylamide (Formula I: R$_2$ is

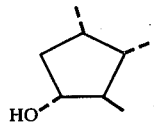

L is —(CH$_2$)$_3$—, Q is

R$_1$ is

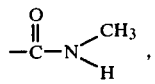

R$_4$ is n-pentyl, V is a valence bond, W is methylene, and X is trans—CH=CH—).

I. Following the procedure of Example 9 but replacing the solution of ammonia in acetonitrile with a solution of methylamine in acetonitrile (3 ml. of a 3 molar solution), there is obtained the corresponding formula-III compound, i.e. (5S,6R)-5-iodo-9-deoxy-6,9α-epoxy-PGF$_1$, methylamide.

II. The title compound is next prepared, following the procedure of Example 2, but replacing the (5S,6R)-5-iodo-9-deoxy-6,9α-epoxy-PGF$_1$, methyl ester starting material of that example with the product of Part I above.

III. Likewise following the procedure of Example 3 but replacing the (5S,6R)-5-iodo-9-deoxy-6,9α-epoxy-PGF$_1$, methyl ester starting material of that example with the product of Part I above, there is also obtained the -formula-I title compound.

EXAMPLE 11

(5E)-9-Deoxy-6,9α-epoxy-Δ$^5$-PGF$_1$, Methyl Ester (Formula I: As defined in Example 1).

Refer to Chart D. A solution of (5Z)-9-deoxy-6,9α-epoxy-Δ$^5$-PGF$_1$, methyl ester (Preparation 2, 4 mg.) in 1 ml. of ethyl acetate (25%)-hexane containing 0.1% triethylamine is treated with iodine (about 1 mg.) and left at about 25° C. for several hours. The reaction mixture is then found to contain the title compound, having R$_f$0.65 (TLC on silica gel in acetone-hexane (1:1).

In a larger preparation the title compound is isolated after silica gel chromatography on preparative TLC plates.

Likewise following the procedures of Example 11 but replacing the (5Z) starting material with the (5E) compound, i.e. (5E)-9-deoxy-6,9α-epoxy-Δ$^5$-PGF$_1$, methyl ester (Example 2), there is obtained an equilibrium mixture of the (5E) and (5Z) compounds from which the (5Z)-9-deoxy-6,9α-epoxy-Δ$^5$-PGF$_1$, methyl ester is isolated.

I claim:

1. A 5E compound of the formula

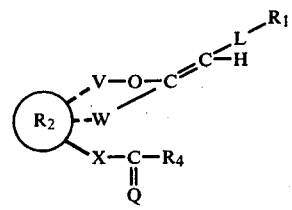

wherein R$_2$ is

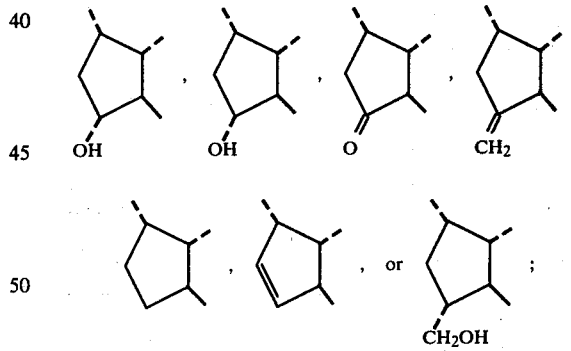

wherein L is
(1) —(CH$_2$)$_d$—C(R$_{22}$)$_2$
(2) —CH$_2$—O—CH$_2$—Y— or
(3) —CH$_2$CH=CH—
wherein d is zero to 5; R$_{22}$ is hydrogen, methyl, or fluoro, being the same or different with the proviso that one R$_{22}$ is not methyl when the other is fluoro; and Y is a valence bond or —(CH$_2$)$_k$— wherein k is one or 2;

wherein Q is

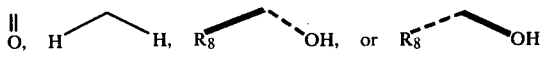

wherein $R_8$ is hydrogen or alkyl of one to 4 carbon atoms, inclusive;

wherein $R_1$ is
(1) —COOR$_3$
(2) —CH$_2$OH
(3) —CH$_2$N(R$_9$)$_2$ (4) 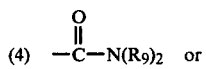 or (5) 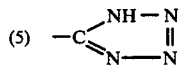

wherein $R_3$ is (a) alkyl of one to 12 carbon atoms, inclusive, (b) cycloalkyl of 3 to 10 carbon atoms, inclusive, (c) aralkyl of 7 to 12 carbon atoms, inclusive, (d) phenyl, (e) phenyl substituted with one, 2, or 3 chloro or alkyl of one to 4 carbon atoms, inclusive;

(f) 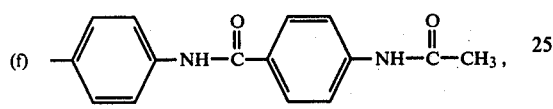

(g) 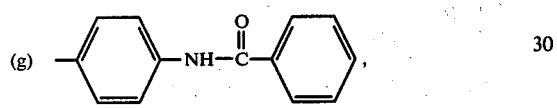

(h) 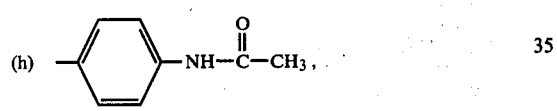

(i) 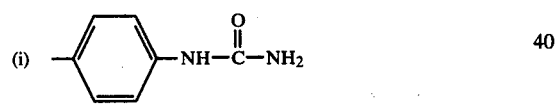

(j) 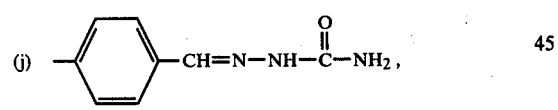

(k) 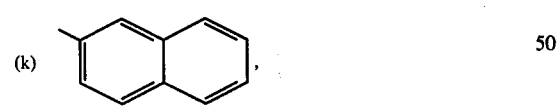

(l) 

wherein $R_{10}$ is phenyl, p-bromophenyl, p-biphenylyl, p-nitrophenyl, p-benzamidophenyl, or 2-naphthyl; and wherein $R_{11}$ is hydrogen or benzoyl;

(m) hydrogen, or (n) a pharmacologically acceptable cation; and wherein $R_9$ is hydrogen or alkyl of one to 4 carbon atoms, inclusive, being the same or different;

wherein $R_4$ is (1) 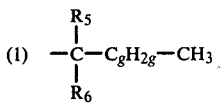

(2) 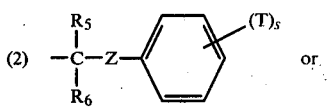 or (3) 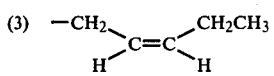

wherein $C_gH_{2g}$ is alkylene of one to 9 carbon atoms, inclusive, with one to 5 carbon atoms, inclusive, in the chain between —CR$_5$R$_6$— and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (-O-); wherein Z represents an oxa atom (-O-) or $C_jH_{2j}$ wherein $C_jH_{2j}$ is a valence bond or alkylene of one to 9 carbon atoms, inclusive with one to 6 carbon atoms, inclusive between CR$_5$R$_6$— and the phenyl ring;

wherein T is alkyl of one to 4 carbon atoms, inclusive, fluoro, chloro, trifluoromethyl, or —OR$_7$— wherein $R_7$ is alkyl of one to 4 carbon atoms, inclusive, and s is zero, one, 2 or 3, with the proviso that not more than two T's are other than alkyl and when s is 2 or 3 the T's are either the same or different;

wherein V is a valence bond; wherein W is —(CH$_2$)$_h$— wherein h is one; and wherein X is
(1) trans—CH=CH—
(2) cis—CH=CH—
(3) —C≡C— or
(4) —CH$_2$CH$_2$—;
including the lower alkanoates thereof.

2. A compound according to claim 1 wherein $R_1$ is

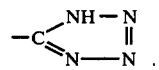

3. A compound according to claim 1 wherein $R_2$ is

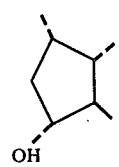

4. A compound according to claim 1 wherein $R_2$ is

5. A compound according to claim 1 wherein (R₂) is

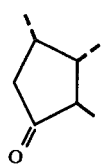

6. A compound according to claim 1 wherein (R₂) is

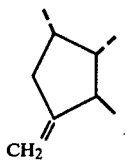

7. A compound according to claim 1 wherein (R₂) is

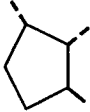

8. A compound according to claim 1 wherein (R₂) is

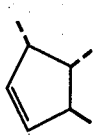

9. A compound according to claim 1 wherein (R₂) is

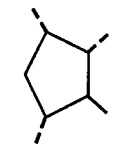

CH₂OH

10. A compound according to claim 3 wherein L is —(CH₂)$_d$—C(R₂₂)₂— wherein d is zero to 5 and R₂₂ is hydrogen, methyl, or fluoro, being the same or different with the proviso that R₂₂ is not methyl when the other is fluoro.

11. A compound according to claim 3 wherein L is —(CH₂)₃— and R₁ is —COOR₃ as defined in claim 3.

12. A compound according to claim 3 wherein L is —CH₂—O—CH₂—Y— wherein Y is a valence bond or (CH₂)$_k$ wherein "k" is one or 2.

13. A compound according to claim 3 wherein L is —CH₂CH=CH—.

14. (5E)-9-Deoxy-6,9α-epoxy-Δ⁵PGF₁, methyl ester, a compound according to claim 11.

15. (5E)-9-Deoxy-6,9α-epoxy-Δ⁵-PGF₁, sodium salt, a compound according to claim 11.

16. A compound according to claim 3 wherein L is —(CH₂)₃— and R₁ is

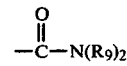

wherein L and R₉ are as defined in claim 1.

17. (5E)-9-Deoxy-6,9α-epoxy-Δ⁵-PGF₁, amide, a compound according to claim 16.

18. (5E)-9-Deoxy-6,9α-epoxy-Δ⁵-PGF₁, methylamide, a compound according to claim 16.

* * * * *

UNITED STATES PATENT OFFICE
CERTIFICATE OF CORRECTION

Patent No. 4,150,222    Dated 17 April 1979

Inventor(s) Roy A. Johnson

It is certified that error appears in the above-identified patent and that said Letters Patent are hereby corrected as shown below:

Cover page, 2nd column, lines 6-8, that portion of the formula should appear as follows:

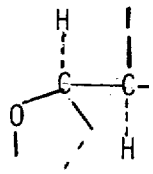

Column 1, lines 67-8, that portion of the formula should appear as follows:

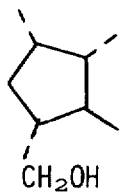

Column 4, line 2, "tha" should read -- that --.
Column 5, line 28, "p-nitroohenyl," should read -- p-nitrophenyl, --.
Column 5, line 64, "triflouromethyl," should read -- trifluoromethyl, --.
Column 7, lines 59-61, that portion of the formula should appear as follows:

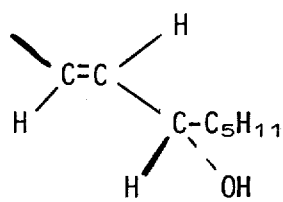

UNITED STATES PATENT OFFICE
CERTIFICATE OF CORRECTION

Patent No. 4,150,222  Dated 17 April 1979

Inventor(s) Roy A. Johnson

It is certified that error appears in the above-identified patent and that said Letters Patent are hereby corrected as shown below:

Column 7, line 65, "-$\Delta^5 PGF_1$." should read -- -$\Delta^5$-$PGF_1$. --.
Column 19, line 30, "cyclopentyl," should read -- cycloheptyl, --.
Column 20, line 8, "...-$CH(CH_3$-." should read -- ...-$CH(CH_3)$-.. --.
Column 20, line 13, "with one of" should read -- with one or --.
Column 22, line 14, "Formula-iv" should read -- Formula-IV --.
Column 22, line 18, "ether us" should read -- ether is --.
Column 22, line 39, "[5.4.0 undecene-5" should read -- [5.4.0] undecene-5 --.
Column 22, line 60, ""Fluorisol" should read -- "Florisil --.
Column 22, line 67, "mterial," should read -- material, --.
Column 23, line 6, "aralyl" should read -- aralkyl --.
Column 23, line 62, "thw" should read -- the --.
Column 24, line 33, "etylamine," should read -- ethylamine, --.
Column 24, line 35, "dedecylamine, allylaine," should read -- dodecylamine, alkylamine, --.
Column 24, line 41, "morphiline," should read -- morpholine, --.
Column 25, line 10, "imprenated" should read -- impregnated --.
Column 28, line 49, "spectrophotometer is" should read -- spectrophotometer in --.
Column 29, line 35, "tital" should read -- title --.
Column 29, line 56, "10 ml.) of" should read -- 10 ml. of --.
Column 29, line 64, "treithylamine" should read -- triethylamine --.
Column 29, line 68, "(1:1), " should read -- (1:1)), --.
Column 30, line 21, "-5Iodo-" should read -- -5-Iodo- --.
Column 30, line 22, "$R_2$," should read -- 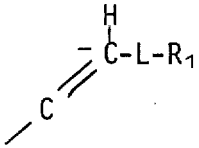 , --.
Column 30, line 58, "-$PGG_2\alpha$" should read -- -$PGF_2\alpha$ --.
Column 32, line 7, "1,5diazabicyclo..." should read -- 1,5-diazabicyclo ... --.
Column 35, line 9, "5S,6R)-" should read -- (5S,6R)- --.
Column 35, line 29, "5S,6R)-" should read -- (5S,6R)- --.
Column 36, line 30, that portion of the formula should appear as follows:

$$\begin{array}{c} \phantom{xx} H \\ \phantom{xx} | \\ -C-L-R_1 \\ /\!\!/ \\ C \\ / \end{array}$$

UNITED STATES PATENT OFFICE
CERTIFICATE OF CORRECTION

Patent No. 4,150,222　　　　　　　　　Dated 17 April 1979

Inventor(s)　　Roy A. Johnson

It is certified that error appears in the above-identified patent and that said Letters Patent are hereby corrected as shown below:

Column 36, line 37, "$R_2$" should read -- 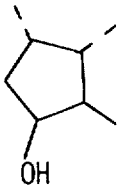 --.
Column 36, line 44, that portion of the formula should appear as follows:

Signed and Sealed this

Twenty-first Day of September 1982

[SEAL]

Attest:

Attesting Officer

GERALD J. MOSSINGHOFF

Commissioner of Patents and Trademarks